United States Patent
Zampieri et al.

(10) Patent No.: US 8,658,662 B2
(45) Date of Patent: Feb. 25, 2014

(54) CRYSTALLINE CDC7 INHIBITOR SALTS

(75) Inventors: Massimo Zampieri, Cesano Maderno (IT); Ermes Vanotti, Milan (IT); Paola Civaroli, Milan (IT); Maria Gioia Fornaretto, Milan (IT)

(73) Assignee: Nerviano Medical Sciences S.r.l., Nerviano (MI) (IT)

(*) Notice: Subject to any disclaimer, the term of this patent is extended or adjusted under 35 U.S.C. 154(b) by 0 days.

(21) Appl. No.: 13/508,648

(22) PCT Filed: Nov. 5, 2010

(86) PCT No.: PCT/EP2010/066873
§ 371 (c)(1),
(2), (4) Date: Jun. 15, 2012

(87) PCT Pub. No.: WO2011/057960
PCT Pub. Date: May 19, 2011

(65) Prior Publication Data
US 2012/0245189 A1    Sep. 27, 2012

(30) Foreign Application Priority Data
Nov. 11, 2009 (EP) .................................. 09175648

(51) Int. Cl.
*A01N 43/54* (2006.01)
*A61K 31/505* (2006.01)

(52) U.S. Cl.
USPC ........................................ 514/275; 544/331

(58) Field of Classification Search
USPC ......................................... 544/331; 514/275
See application file for complete search history.

(56) References Cited

FOREIGN PATENT DOCUMENTS

| WO | WO 2007/110344 A1 | 10/2007 |
| WO | WO 2007110344 A1 * | 10/2007 |
| WO | WO 2009/133170 A1 | 11/2009 |
| WO | WO 2009133170 A1 * | 11/2009 |

OTHER PUBLICATIONS

S.L. Morissette et al., Advanced Drug Delivery Reviews, 56, 275-300 (2004).*
L.D. Bighley et al., Salt Forms and Absorption, in 13 Encyclopedia of Pharmaceutical Technology 453 (M Swarbrick and J. Boylan eds., 1996).*
iS.L. Morissette et al., Advanced Drug Delivery Reviews, 56, 275-300 (2004).*
Caira M.R., "Crystalline Polymorphism of Organic Compounds", *Topics in Current Chemistry* 198:163-208 (Jan. 1, 1998).
Hilfiker R. et al., "Polymorphism in the Pharmaceutical Industry", *Hilfiker R (Editor) Ed*, pp. 1-19 (Jan. 1, 2006).
Harwood L.M. et al., "Experimental Organic Chemistry-Principles and Practice", *Experimental Chemistry—Organic Chemistry and Reaction*, pp. 127-132 (Jan. 1, 1989).
Anderson et al., "Tools for Purifying the Product: col. Chromatography, Crystallization and Reslurrying", *Practical Process Research and Development*, pp. 223-247 (Jan. 1, 2000).
Byrn S. et al., "Pharmaceutical Solids: A Strategic Approach to Regulatory Considerations", *Pharmaceutical Research* 12(7):945-954 (Jul. 1, 1995).
International Search Report dated Feb. 28, 2011 received from the European Patent Office from related International Application No. PCT/EP2010/066873.

* cited by examiner

*Primary Examiner* — James O Wilson
*Assistant Examiner* — Alexander R Pagano
(74) *Attorney, Agent, or Firm* — Scully, Scott, Murphy & Presser, P.C.

(57) ABSTRACT

The present invention relates to novel crystalline salts of a CDC7 or CDC7/CDKs inhibitor, to a novel crystal form of the corresponding free base, to a process for their preparation, to hydrates, solvates and polymorphs of such new salt forms, to their use in therapy and to pharmaceutical compositions containing them. Such crystal salts are selected from L-asparate, hemifumarate, hydrochloride, maleate, mesylate, sulfate, L-tartrate or phosphate salts of 5-(2-amino-pyrimidin-4-yl)-2-(2,4-dichloro-phenyl)-1H-pyrrole-3-carboxylic acid amide.

6 Claims, 6 Drawing Sheets

CRYSTALLINE CDC7 INHIBITOR SALTS

The present invention relates to novel crystalline salts of a CDC7 or CDC7/CDKs inhibitor, to a novel crystal form of the corresponding free base, to a process for their preparation, to hydrates, solvates and polymorphs of such new crystalline salt forms, to their use in therapy and to pharmaceutical compositions containing them. WO 2007110344, filed in the name of the present applicant, describes and claims heteropentacycles, processes for their preparation, pharmaceutical compositions comprising them and their use as therapeutic agents, particularly in the treatment of cancer and cell proliferation disorders. Representative heteropentacycle compounds, optionally in the form of pharmaceutically acceptable salts, are for example:

5-(2-amino-pyrimidin-4-yl)-2-phenyl-1H-pyrrole-3-carboxylic acid amide;
5-(2-amino-pyrimidin-4-yl)-2-o-tolyl-1H-pyrrole-3-carboxylic acid amide;
5-(2-amino-pyrimidin-4-yl)-2-(4-fluoro-2-methyl-phenyl)-1H-pyrrole-3-carboxylic acid amide;
5-(2-amino-pyrimidin-4-yl)-2-(2,3-dimethyl-phenyl)-1H-pyrrole-3-carboxylic acid amide;
5-(2-amino-pyrimidin-4-yl)-2-(2,3-difluoro-phenyl)-1H-pyrrole-3-carboxylic acid amide;
5-(2-amino-pyrimidin-4-yl)-2-(2,4-difluoro-phenyl)-1H-pyrrole-3-carboxylic acid amide;
5-(2-amino-pyrimidin-4-yl)-2-(2,5-difluoro-phenyl)-1H-pyrrole-3-carboxylic acid amide;
5-(2-amino-pyrimidin-4-yl)-2-(2-chloro-phenyl)-1H-pyrrole-3-carboxylic acid amide;
5-(2-amino-pyrimidin-4-yl)-2-(2-chloro-4-fluoro-phenyl)-1H-pyrrole-3-carboxylic acid amide;
5-(2-amino-pyrimidin-4-yl)-2-(2,4-dichloro-phenyl)-1H-pyrrole-3-carboxylic acid amide;
5-(2-amino-pyrimidin-4-yl)-2-(2-fluoro-4-methyl-phenyl)-1H-pyrrole-3-carboxylic acid amide;
5-(2-amino-pyrimidin-4-yl)-2-(2,3-dichloro-phenyl)-1H-pyrrole-3-carboxylic acid amide;
5-(2-amino-pyrimidin-4-yl)-2-(2-fluoro-3-methoxy-phenyl)-1H-pyrrole-3-carboxylic acid amide and
5-(2-amino-pyrimidin-4-yl)-2-(2-fluoro-4-chloro-phenyl)-1H-pyrrole-3-carboxylic acid amide.

Such compounds are endowed with protein kinase inhibiting activity and, more particularly, CDC7 or CDC7/CDKs inhibiting activity. The compounds are also active as inhibitors of other protein kinases and thus be effective in the treatment of diseases associated with other protein kinases.

More specifically, such compounds invention are useful in the treatment of a variety of cancers and of cell proliferative disorders.

These compounds, and analogues thereof, can be for instance prepared as described in the above mentioned patent application WO 2007110344.

However, the above-mentioned patent application discloses only some specific salt forms of the compounds exemplified therein, and no reference to any crystal form of free base or salt is described.

It has now unexpectedly been found that some specific pharmaceutically acceptable salts of one specific compound therein described have a number of advantages over the known free base form and, additionally, such salts were unexpectedly found to have a unique combination of good formulation properties which make them particularly suitable for the preparation of pharmaceutical formulations.

As a matter of fact, although the specific compound therein described is as effective as the free base, practically it can be best administered in the crystalline salt form of some acids or of the free base.

Therefore, it is an object of the invention to provide, in a first aspect, specific crystalline salts of one of the compounds described in the above mentioned patent application of the formula:

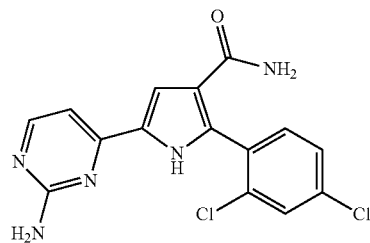 [SMILES: NC(=O)c1cc(-c2ccnc(N)n2)[nH]c1-c1ccc(Cl)cc1Cl]

and with chemical name:
5-(2-amino-pyrimidin-4-yl)-2-(2,4-dichloro-phenyl)-1H-pyrrole-3-carboxylic acid amide or
1H-pyrrole-3-carboxamide, 5-(2-amino-4-pyrimidinyl)-2-(2,4-dichlorophenyl).

In the present application, unless otherwise specified, such compound is coded NMS-E354.

Therefore, the present invention relates to crystalline hemifumarate salt, maleate salt, hydrochloride salt, mesylate salt, sulfate salt, L-aspartate salt, L-tartrate salt or phosphate salt of NMS-E354, or their hydrates, solvates and polymorphs.

The preferred crystalline salts of the present invention are hemifumarate, maleate, mesylate and sulfate salts of NMS-E354. The present invention in particular relates to new crystalline forms, solvates and hydrates of NMS-E354 maleate and sulfate salt, more preferably to maleate salt. Preferably, the invention relates to crystalline NMS-E354 maleate and sulfate salts, even more preferably to crystalline maleate salt.

As stated above, the present invention relates also to new crystalline forms of NMS-E354 free base.

The preparation of NMS-E354 is described in the above mentioned International Patent Application WO 2007110344. In particular, NMS-E354 is prepared as free base according to the synthetic procedure of Example 19, step 3 of that application, wherein essentially a suitable carboxylic acid derivative is condensed with an activated form of ammonia to give the desired amide. Such carboxylic acid derivative, in its turn, is prepared according to a procedure of Example 19, steps 1 and 2, comprising the coupling of a haloketone with a beta-ketoester, a Hantzsch reaction and a hydrolysis.

An alternative process for the preparation of NMS-E354 is described in the International Patent Application WO 2009 133170 in the name of the present applicant, step IV of Example 1, comprising the hydrolysis of a suitable nitrile derivative in acidic condition and the subsequent treatment with a base.

NMS-E354 as free base is a poorly water-soluble compound, which shows aqueous solubility lower than 0.01 mg/ml. The solubility of the NMS-E354 free base is about 4 mg/ml in 10% Polysorbate 80 in 5% dextrose solution, about 7 mg/ml in aqueous 50% Polyethylene Glycol 400 in 5% dextrose solution and about 1÷2 mg/ml when formulated as hydrochloride or phosphate in situ salt. NMS-E354 free base was also suitable for aqueous hypromellose suspensions at about 10 mg/ml. Therefore, the obtained free base was initially formulated as cosolvent based aqueous solution, in situ salt or hypromellose suspension in order to allow administration during early pharmacological and toxicological evaluation for early pharmacological studies.

Though solving the problem of the early formulation approach, the applied formulation approaches were not suitable for development of an oral formulation suitable for the desired final therapeutic uses in clinic.

Moisture uptake is a significant concern for pharmaceutical powders. Moisture has been shown to have a significant impact, for example, on the physical, chemical and manufacturing properties of drugs, excipients and formulations. It is also a key factor in taking decisions related to packaging, storage, handling and shelf life and successful development requires a sound understanding of hygroscopic properties.

For instance, conversion from an anhydrous to a hydrate form may be observed when the relative humidity exceeds a critical level and moisture content rapidly increases in the solid. This has not only an impact on the physical and pharmaceutical properties of the drug per se, but also on its biopharmaceutical perspective. Moreover, it is well known, that hydrate forms usually tends to be less soluble with respect to a homologous anhydrous form, with potential detrimental effect also on the dissolution rate properties of the active compound per se and on its absorption profile through the gastrointestinal tract. At the same manner, conversion from a crystalline to an amorphous form may be observed in presence of humidity, with potential disadvantages in terms of physical stability. The amorphous active drug substance, if deliquescent, can for instance absorb relatively large amounts of water from the atmosphere up to its dissolution while also its chemical stability can be affected since the amorphous structure, being thermodynamically activated, is more prone to chemical degradation and to chemical interaction with other chemical species. Thus the performance and the efficacy of both formulation and active ingredient may be significantly changed.

Frequently, salts shows higher hygroscopicity than the free base.

In addition, in order to have the desired therapeutic effect the drugs should have a good pharmacokinetic behaviour, in particular should show good bioavailability. Bioavailability captures two essential features, namely the maximum plasma concentration ($C_{max}$) and the systemic exposure (AUC). As it is well known by the skilled person, the maximum plasma concentration means how much of the nominal strength of the drug enters the body (extent of absorption); the systemic exposure means how fast the drug enters the systemic circulation (rate of absorption). Given that the therapeutic effect is function of the drug concentration in the patient's blood, these two properties of non-intravenous dosage-forms are, in principle, important in identifying the response to a drug dose. Bioavailability following oral doses may vary also because of patient related factors, such as nature and timing of meals, age, disease, genetic traits and gastrointestinal physiology.

Accordingly, there was a strong need in therapy of a form of NMS-E354 endowed with an improved water-solubility, low hygroscopicity and good and reproducible biopharmaceutical properties so that to allow a safer and efficacious administration in comparison with the free base.

As it is well known by the skilled person, salt formation does not always result in an enhancement of solubility characteristics (see for instance: Shozo Miyazaki, et al., International Journal of Pharmaceutics 1980; 6(1), 77-85) as well as the behavior of the different salts in terms of solubility and/or dissolution and/or sensitivity to counter-ion effect can be different according to the properties of each drug-counterion couple.

Surprisingly, the present inventors have solved the above-described technical problem by providing novel salts as well as novel crystalline forms of salts of NMS-E354 having improved physicochemical and pharmacokinetic properties.

In fact, the novel salts are crystalline, rapidly-dissolving solids with high water solubility; moreover these salts are low or moderately hygroscopic, thus substantially introducing important advantages in handling, storage and formulations etc; finally, these salts have a pharmacokinetic profile surprisingly better than that of the freebase in addition to possessing all the other advantages, in particular therapeutic advantages, exhibited by the free base when formulated as in situ salt or methocel suspension.

Surprisingly, new forms of NMS-E354 salts, as well as of the free base, were found and proven to be crystalline. Unexpectedly, the salts of the present invention are of low hygroscopicity, comparable to that of the known free base.

Therefore, the present inventors have solved the above-described technical problem by providing novel crystal form of salts of NMS-E354, as well as crystal forms of the free base, having improved physicochemical properties. In fact, the novel salts are crystalline, non hygroscopic solids with adequate water solubility and substantially introducing important advantages in handling, storage and formulations etc., in addition to possessing all the other favourable properties, in particular therapeutic favourable properties, exhibited by the free base when formulated as cosolvent based aqueous solution, in situ salt or hypromellose suspension.

The property of being crystalline powders renders these forms particularly suitable for pharmaceutical development.

BRIEF DESCRIPTION OF THE DRAWINGS

The invention is also illustrated by reference to the accompanying drawings described below.

Figure 1:
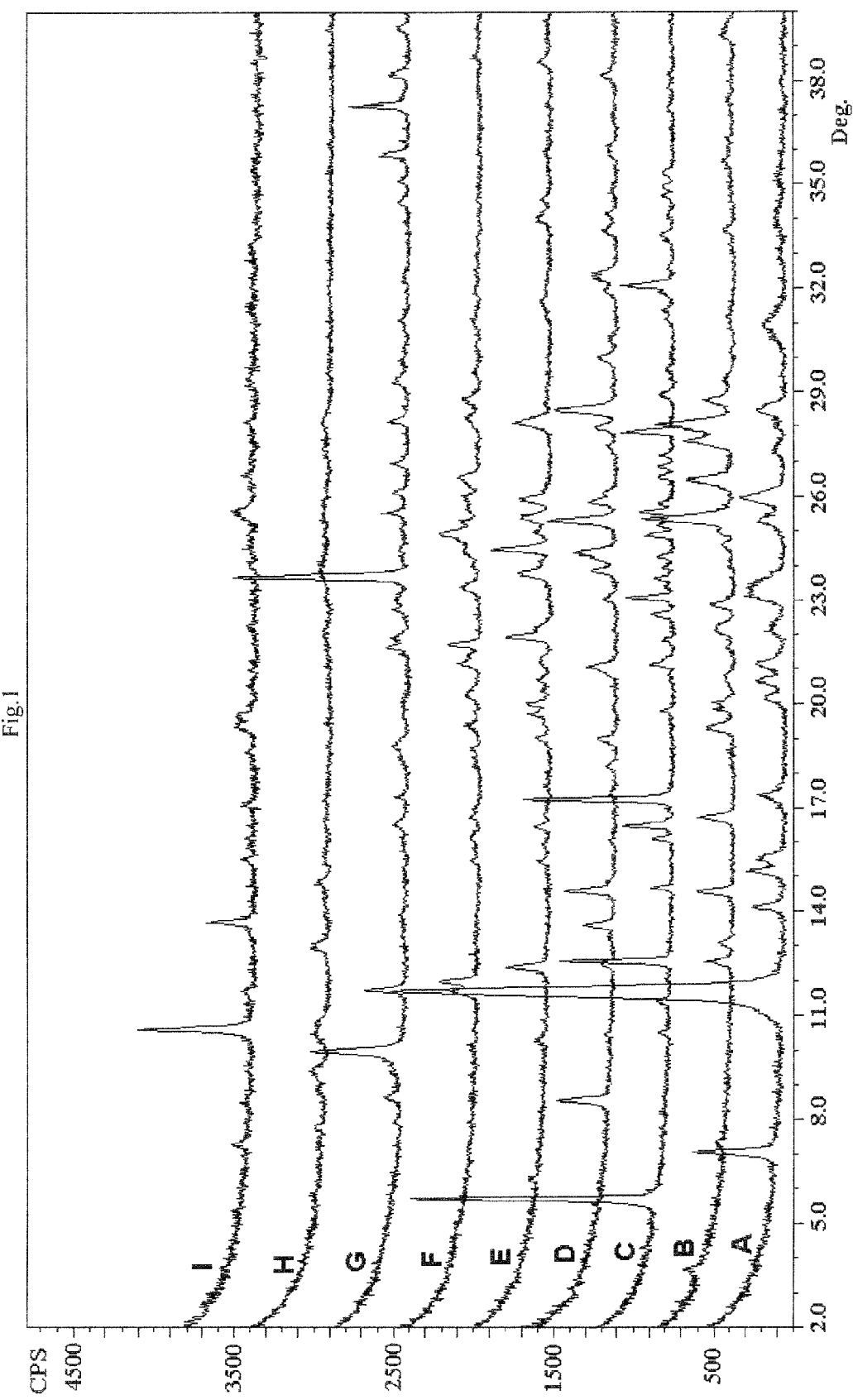
FIG. 1 shows the X-ray diffractograms of NMS-E354 free base form I (A), hemifumarate form I (B), maleate form I (C), hydrochloride form I (D), mesylate form I (E), sulfate form I (F), L-aspartate form I (G), L-tartrate form I (H), phosphate form I (I) salts, prepared according to examples 1 to 3. The X-ray diffractogram graph reports 2-theta angles (deg) on the x axis while intensity (CPS) is reported on the y axis.

Such salts of NMS-E354 can be obtained by known analogy methods by means of the desired stoichiometric addition of solvent or aqueous solutions of the counterion to the free base dissolved in a suitable solvent. Such solvent is water or an organic, in particular anhydrous, solvent chosen preferably from methanol, ethanol and their mixtures. If necessary, the precipitation or the crystallization of the obtained salt may be favoured by addition or reworking in an anhydrous apolar solvent, for instance diethylether, n-hexane or cyclohexane.

In particular, an aliquot of NMS-E354 free base may be dissolved at room temperature in a suitable amount of suitable solvent, obtaining a desired nominal concentration. Salt formation can then be performed by addition of appropriate amounts of the counterions to the NMS-E354 free base solution so prepared at the same temperature. Crystallizations are performed by cooling and maintaining subsequently the solution for adequate resting times.

The free base used as starting material can be one prepared as set forth in the above cited International Applications, or a crystalline form (I) prepared as described below.

The obtained precipitates are collected by vacuum filtration and dried. To favour the crystallization, the solutions can be optionally concentrated by evaporation. A further step of re-crystallization (e.g. compound triturated in an anhydrous apolar solvent such as diethylether) can be carried out to isolate the desired crystalline form. Chemical identification of NMS-E354 and acidic counterion can be performed by $^1$H NMR.

In another aspect, the present invention relates to new crystalline forms of NMS-E354 free base, that can be prepared starting from the known form, using analogous procedure of crystallization in an appropriate solvent followed from isolation and drying of the desired crystalline form.

According to the present invention, the definition of crystalline salts and free base also comprises hydrates, solvates and polymorphs thereof.

A further object of the invention is to provide a pharmaceutical composition comprising a crystalline form, solvate or hydrate of any salt or free base of NMS-E354 as above defined, preferably of the maleate or sulphate salt, even more preferably of the maleate salt, as active ingredient and a pharmaceutically acceptable excipient and/or carrier.

A further object of the invention is to provide a crystalline form, solvate or hydrate of any salt or free base of NMS-E354 as above defined, preferably of the maleate or sulphate salt, even more preferably of the maleate salt, for the use as a medicament, in particular as a CDC7 or CDC7/CDKs inhibitor.

A further object of the invention is to provide a crystalline form, solvate or hydrate of any salt or free base of NMS-E354 as above defined, preferably of the maleate or sulphate salt, even more preferably of the maleate salt, for use in treating a mammal, comprising a human being, suffering from a disease state treatable by CDC7 or CDC7/CDKs inhibition.

A further object of the invention is to provide a method for treating a mammal, including a human being, in need of CDC7 or CDC7/CDKs inhibition, comprising administering to said mammal a therapeutically effective amount of a crystalline form, solvate or hydrate of any salt or free base of NMS-E354 as above defined, preferably of the maleate or sulphate salt, even more preferably of the maleate salt.

Additionally, the present invention relates to a crystalline form, solvate or hydrate of any salt or free base of NMS-E354 as above defined, preferably of the maleate or sulphate salt, even more preferably of the maleate salt, for the treatment of a mammal, comprising a human being, suffering from a disease state treatable by CDC7 or CDC7/CDKs inhibition, that means cell proliferative disorders such as cancer, viral infections, auto-immune diseases and neurodegenerative disorders.

Accordingly, a crystalline form, solvate or hydrate of any salt of or free base of NMS-E354 as above defined, preferably of the maleate or sulphate salt, even more preferably of the maleate salt, either alone or in association with other therapeutic agents, is useful for treating a mammal, comprising humans, suffering from a disease state treatable by CDC7 or CDC7/CDKs inhibition, or in the preparation of a medicament for such treatment.

Therefore, the present invention also provides the use of a crystalline form, solvate or hydrate of any salt or free base of NMS-E354 as above defined, preferably of the maleate or sulphate salt, even more preferably of the maleate salt, for the manufacture of a medicament for the treatment of a disease state treatable by CDC7 or CDC7/CDKs inhibition.

The term "disease state treatable" means that the treatment according to the invention provides remission or stabilization of the disease state or at least the conditions and quality of life of the mammal under treatment are improved. More specifically, the compounds of this invention are useful in the treatment of a variety of cancers including, but not limited to: carcinoma such as bladder, breast, colon, rectum, kidney, liver, lung, including small cell lung cancer, esophagus, gallbladder, ovary, pancreas, stomach, cervix, thyroid, prostate, and skin, including squamous cell carcinoma; hematopoietic tumors of lymphoid lineage, including leukemia, acute and chronic lymphoblastic leukemia, Hodgkin's lymphoma, non-Hodgkin's lymphoma, Burkitt's lymphoma and multiple myeloma; hematopoietic tumors of myeloid lineage, including acute and chronic myelogenous leukemias, myelodysplastic syndrome; tumors of mesenchymal origin, including fibrosarcoma and rhabdomyosarcoma; tumors of the central and peripheral nervous system, including astrocytoma, neuroblastoma, glioma and schwannomas; other tumors, including melanoma, seminoma, teratocarcinoma, osteosarcoma, xeroderma pigmentosum, keratoxanthoma, thyroid follicular cancer and Kaposi's sarcoma.

Due to the key role of protein kinases, and, in particular, of CDC7 or CDKs in the regulation of cellular proliferation, these heteropentacycles are also useful in the treatment of a variety of cell proliferative disorders such as, for instance, benign prostate hyperplasia, familial adenomatosis, polyposis, neuro-fibromatosis, psoriasis, vascular smooth cell proliferation associated with atherosclerosis, pulmonary fibrosis, arthritis glomerulonephritis and post-surgical stenosis and restenosis.

The effective dose crystalline salts and free base of NMS-E354 may vary according to the disease, severity of the disorder and the conditions of the patient to be treated. Therefore the physician, as always, must set the optimal dose for each patient. Anyway, the effective dosage range may be from about 10 to about 1000 mg per dose, from 1 to 10 times daily, preferably from about 20 mg/m²/day to about 200 mg/m²/day (calculated as free base), either as a single or multiple divided daily dosages. For example, the compound can be orally administered for seven or fourteen consecutive days every respectively two or three weeks.

A crystalline form, solvate or hydrate of any salt or free base of NMS-E354 as above defined, preferably of the maleate or sulphate salt, even more preferably of the maleate salt, is readily orally absorbed, therefore it is preferably orally administered. Needless to say, the compounds of the present invention may be also administered by any other administration route, for instance by parenteral, topical, rectal and nasal route.

NMS-E354 preferred hemifumarate, maleate, mesylate, sulfate salts are substances showing low hygroscopicity and high melting behavior.

NMS-E354 salts show improved aqueous solubility in comparison with the free base, for example the solubility of the maleate and sulfate salts in 0.9% NaCl solution is respectively 0.07 to 0.15 mg/ml.

Besides the advantage of exhibiting improved water solubility, the NMS-E354 salts, in particular maleate and sulfate salts, are also particularly suitable to be manufactured reproducibly in a clear acid/base ratio.

This finding renders these salts particularly suitable for the use in liquid formulations for oral as well as for intravenous formulations.

In another preferred embodiment, the form I of the essentially pure 1:1 sulfate salt of NMS-E354 shows the X-ray diffraction diagram indicated in FIG. 2E.

High preference is also given for the form I of the 1:1 sulfate salt of NMS-E354 which shows an X-ray diffraction diagram of the type shown in FIG. 2E, with peak intensities at the 2-theta values (deg) described in table 1 above.

In samples being free of any additional materials (other crystal forms, excipients), it should be possible to observe diffraction peaks at about the 2-theta values (deg) described in table 3 below.

In another preferred embodiment, the form I of the essentially pure 1:1 mesylate salt of NMS-E354 shows the X-ray diffraction diagram indicated in FIG. 2D.

High preference is also given for the form I of the 1:1 mesylate salt of NMS-E354 which shows an X-ray diffraction diagram of the type shown in FIG. 2D, with peak intensities at the 2-theta values (deg) described in table 1 above.

In samples being free of any additional materials (other crystal forms, excipients), it should be possible to observe diffraction peaks at about the 2-theta values (deg) described in table 4 below.

In another preferred embodiment, the form I of the essentially pure hemifumarate salt of NMS-E354 shows the X-ray diffraction diagram indicated in FIG. 2C.

High preference is also given for the form I of the hemifumarate salt of NMS-E354 which shows an X-ray diffraction

TABLE 1

Solid state properties of crystal forms of representative salts and free base of NMS-E354.

| Crystal form of NMS-E354 | PXRD FIG. | PXRD Table | Significant PXRD peaks (2-theta, deg) (**) | DSC FIG. |
|---|---|---|---|---|
| Maleate salt * | 1C, 2B, 3 | 2 | 5.8, 10.6, 12.6, 14.7, 16.1, 16.6, 17.4, 21.2, 22.6, 23.7, 25.0, 25.2, 25.6, 27.9, 32.2 | 4C, 5B, 6 |
| Sulfate salt * | 1F, 2E | 3 | 12.0, 12.3, 16.2, 16.7, 18.5, 20.5, 21.8, 23.4, 24.8, 25.3, 26.5, 28.1, 28.8, 31.1, 38.7 | 4F, 5E |
| Mesylate salt * | 1E, 2D | 4 | 12.4, 16.5, 19.0, 19.7, 20.0, 21.9, 22.2, 23.8, 24.5, 25.0, 25.4, 25.9, 28.1, 34.1, 38.6 | 4E, 5D |
| Hemifumarate salt * | 1B, 2C | 5 | 3.6, 7.3, 12.5, 13.1, 14.5, 16.7, 19.3, 22.2, 22.9, 25.3, 26.4, 27.6, 28.0, 28.7, 39.3 | 4B, 5C |
| Free base | 1A, 2A | 6 | 7.1, 11.7, 14.1, 15.2, 15.5, 17.3, 20.2, 20.7, 21.2, 23.1, 23.4, 25.3, 26.0, 28.5, 30.9 | 4A, 5A |

Note *: Form I, if not differently specified, the described salts are intended in the 1:1 molar ratio between the free base and counterion.
Note (**): The reported PXRD (meaning defined below) peaks have been selected according to their higher intensity among the complete dataset described in the specified PXRD Table.

The references in the 2$^{nd}$ and 5th columns and are formed from:
- the number of the pertinent PXRD and DSC figures
- a capital letter that identifies the curve if there are more than one in the figures.

The same type of reference is used all over the present specification, unless otherwise specified. In a preferred embodiment, the form I of the essentially pure 1:1 maleate salt of NMS-E354 shows the X-ray diffraction diagram indicated in FIG. 3.

Figure 3:
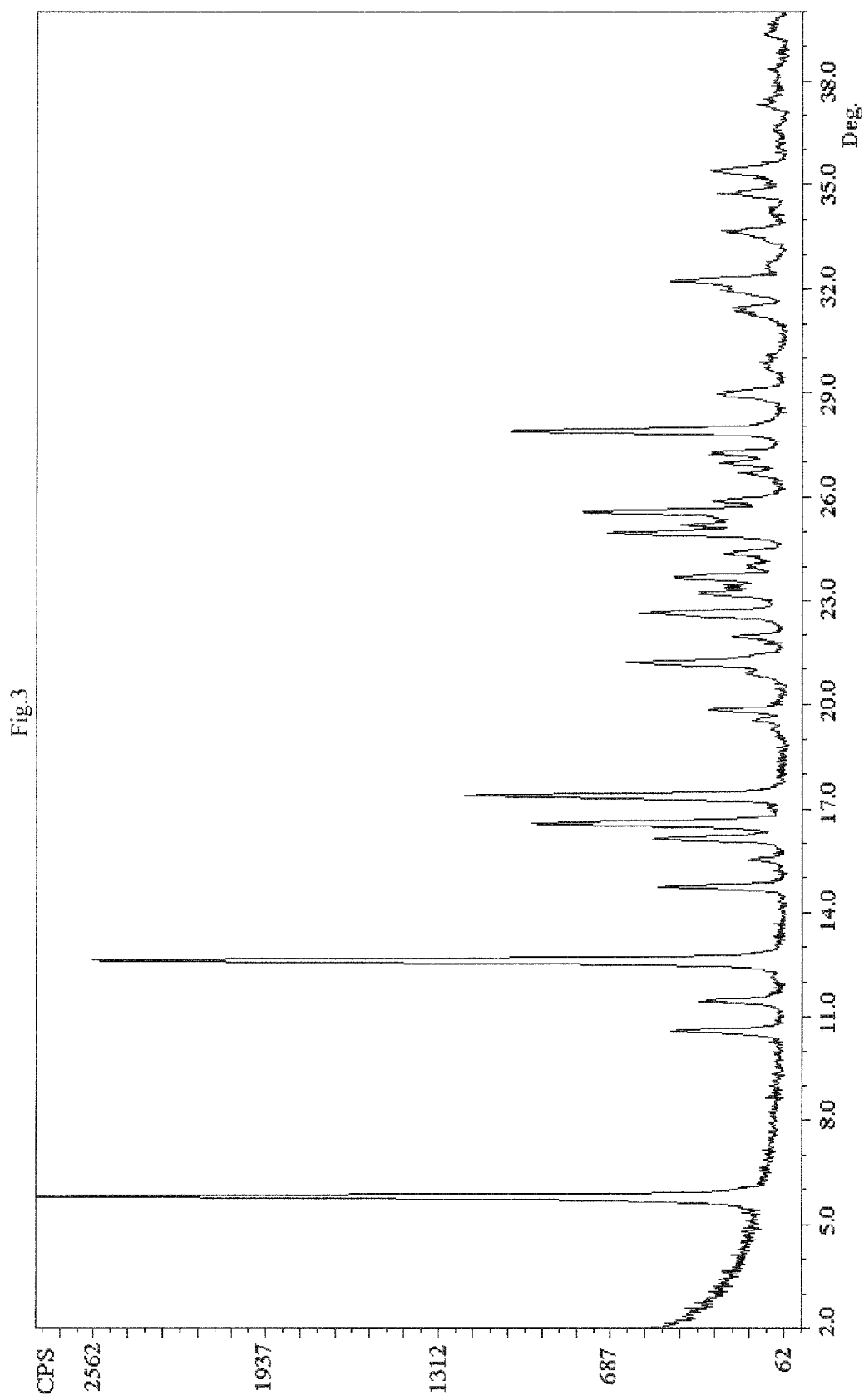
FIG. 3 shows the X-ray diffractogram of NMS-E354 maleate salt form I prepared according to example 5. The X-ray diffractogram graph reports 2-theta angles (deg) on the x axis while intensity (CPS) is reported on the y axis.
Figure 4:
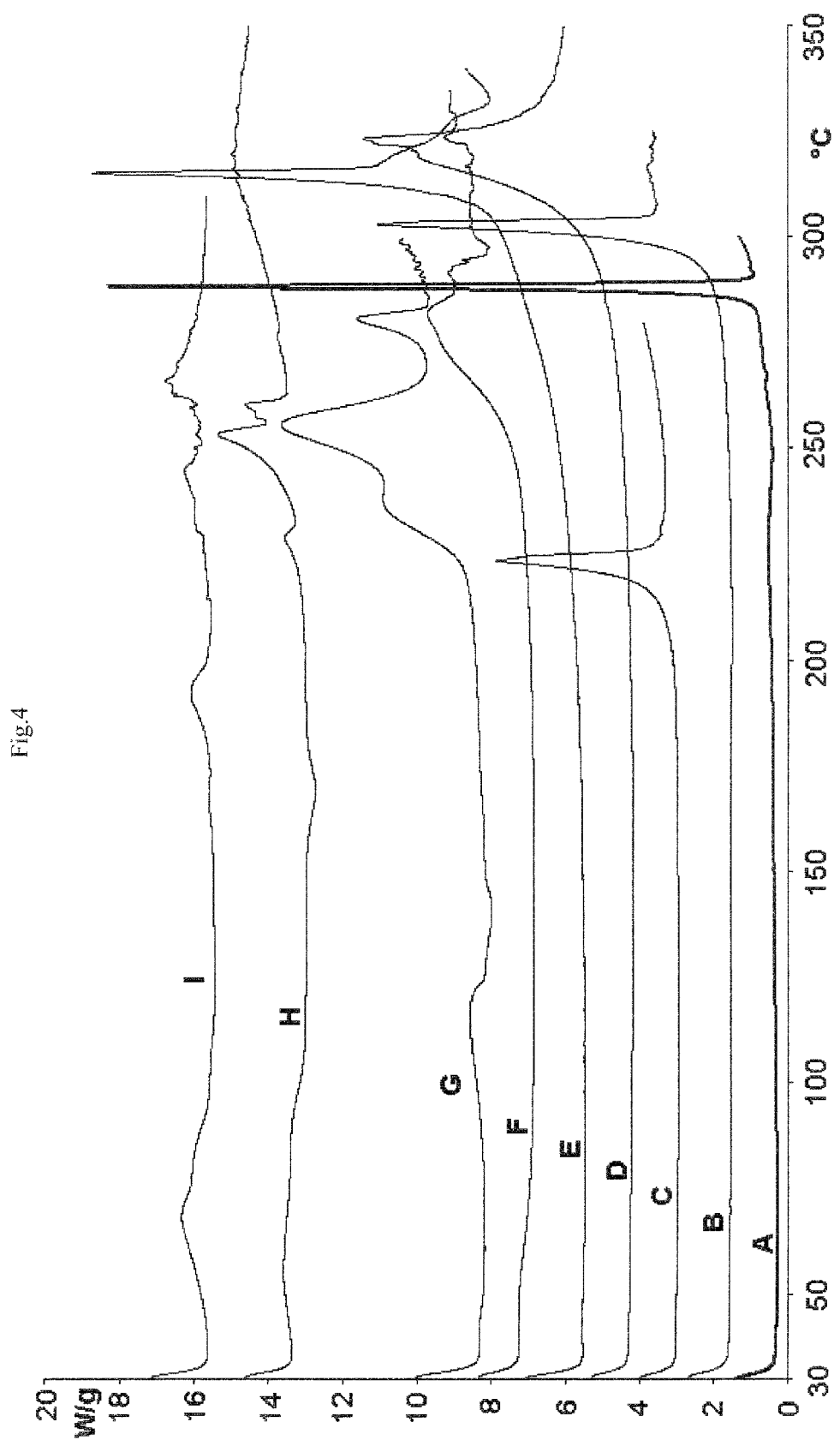
FIG. 4 shows the DSC (Differential Scanning calorimetry) thermograms of crystalline NMS-E354 free base form I (A), hemifumarate form I (B), maleate form I (C), hydrochloride form I (D), mesylate form I (E), sulfate form I (F), L-aspartate form I (G), L-tartrate form I (H), phosphate form I (I) salts, prepared according to examples 1 to 3. The thermogram reports temperature (° C.) on the x axis while normalized heat flow (W/g) is reported on the y axis.
Figure 5:
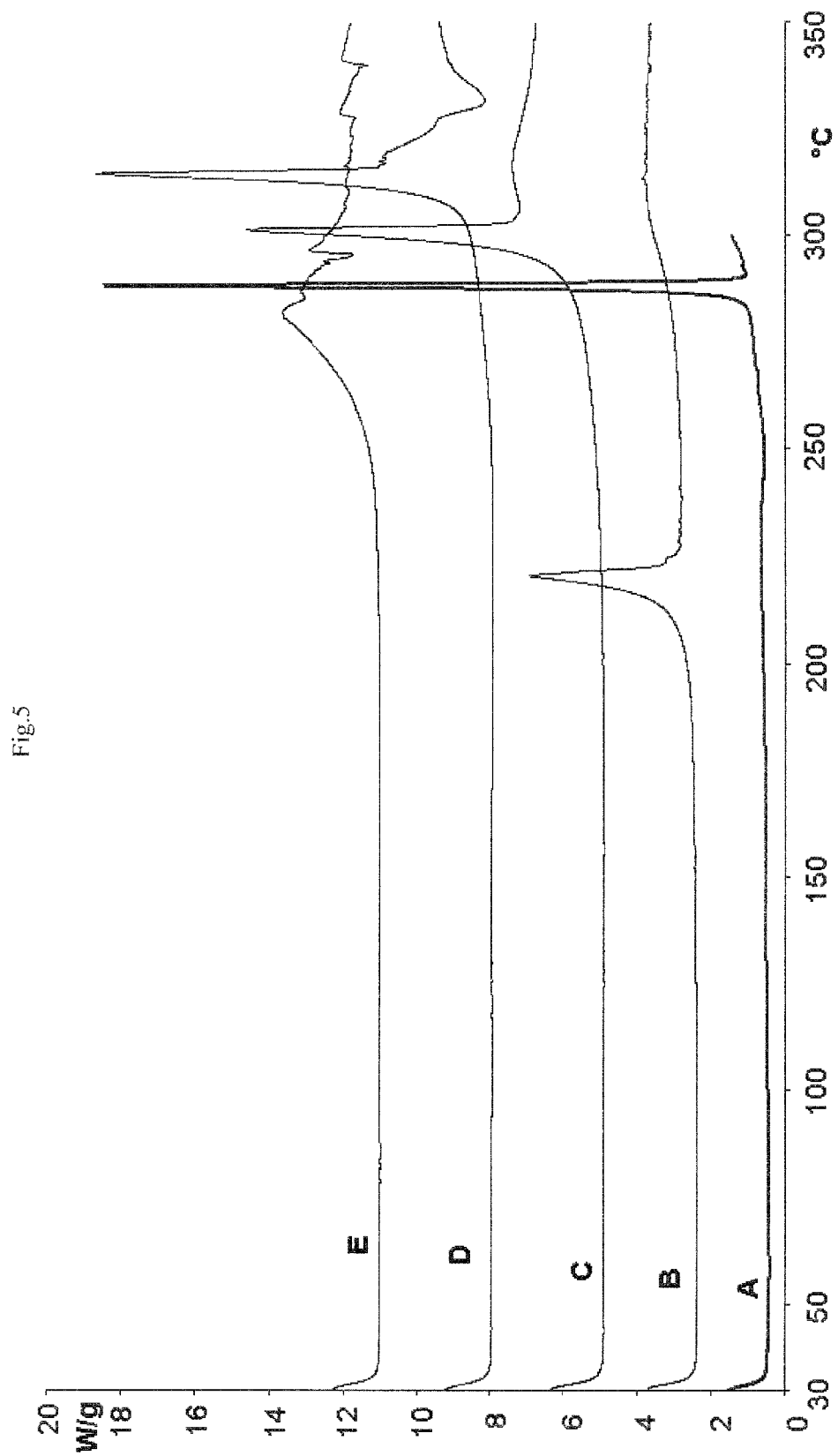
FIG. 5 shows the DSC thermograms of NMS-E354 free base form I (A), prepared according to example 1, and maleate form I (B), hemifumarate form I (C), mesylate form I (D), sulfate form I (E) salts prepared according to example 4. The thermogram reports temperature (° C.) on the x axis while normalized heat flow (W/g) is reported on the y axis.

High preference is also given for the form I of the 1:1 maleate salt of NMS-E354 which shows an X-ray diffraction diagram of the type shown in FIG. 3, with significant peak intensities at the 2-theta values (deg) described in table 1 above.

In samples being free of any additional materials (other crystal forms, excipients), it should be possible to observe diffraction peaks at about the 2-theta values (deg) described in table 2 below.

diagram of the type shown in FIG. 2C, with peak intensities at the 2-theta values (deg) described in table 1 above.

In samples being free of any additional materials (other crystal forms, excipients), it should be possible to observe diffraction peaks at about the 2-theta values (deg) described in table 5 below.

In another preferred embodiment, the crystal form I of the essentially pure NMS-E354 free base shows the X-ray diffraction diagram indicated in FIG. 2A.

High preference is also given for the form I of the NMS-E354 free base which shows an X-ray diffraction diagram of the type shown in FIG. 2A, with peak intensities at the 2-theta values (deg) described in table 1 above.

In samples being free of any additional materials (other crystal forms, excipients), it should be possible to observe diffraction peaks at about the 2-theta values (deg) described in table 6 below.

Essentially pure means that the crystal forms of the present invention have a purity of at least 90%. More preferably the crystal forms of the present invention have a purity of at least 95%, and most preferably at least 99% by weight of the crystals of an acid addition salt or free base of NMS-E354 are present in the crystal form according to the invention.

Solubility of Crystalline NMS-E354 Salts and Free Base

The determination of solubility of NMS-E354 salts has been performed by means of the following procedure: known amounts of crystalline NMS-E354 salts or free base stirred for 4 hours at RT in 0.9% NaCl solution, in condition of excess solid considering a target concentration of 10 mg/ml. The obtained preparations were filtered and analysed by means of HPLC. The results are here below reported in Table 1a.

TABLE 1a

Solubility of crystal forms of representative salts and free base of NMS-E354.

| Crystal form of NMS-E354 | Aqueous solubility value |
| --- | --- |
| Maleate salt | 0.07 mg/mL |
| Sulfate salt | 0.15 mg/mL |
| Mesylate salt | 0.12 mg/mL. |
| Hemifumarate salt | 0.02 mg/mL |
| Free base | <0.01 mg/mL |

Analytical Results by Means of Powder X-Ray Diffraction (PXRD)

The NMS-E354 salts were characterized by powder X-Ray Diffraction (PXRD) performed using a Thermo/ARL XTRA apparatus, irradiating powder samples with a CuKα source (45 kV, 40 mA, 1.8 kW–Kα1 radiation, wavelength λ=1.54060 Angstrom) between 5° and 40° 2-theta at room temperature.

The scan rate was of 1.20°/min (0.020° step with count time of 1 seconds per step).

In the X-Ray diffractograms, the angles of diffraction 2-theta are plotted on the horizontal axis α-axis) and the line intensity on the vertical (y-axis).

In the paragraphs defining the X-ray powder diffraction peaks for the crystalline forms of the salts and free base of NMS-E354, the term 'at about' is used in the expression ' . . . at about the 2-theta angles reported in table . . . ' to indicate that the precise position of peaks (i.e. the recited 2-theta angle values) should not be construed as being absolute values because, as will be appreciated by those skilled in the art, the precise position of the peaks may vary slightly between one machine and another, from one sample to another, or as a result of slight variations in the applied measurement conditions.

Figure 2:
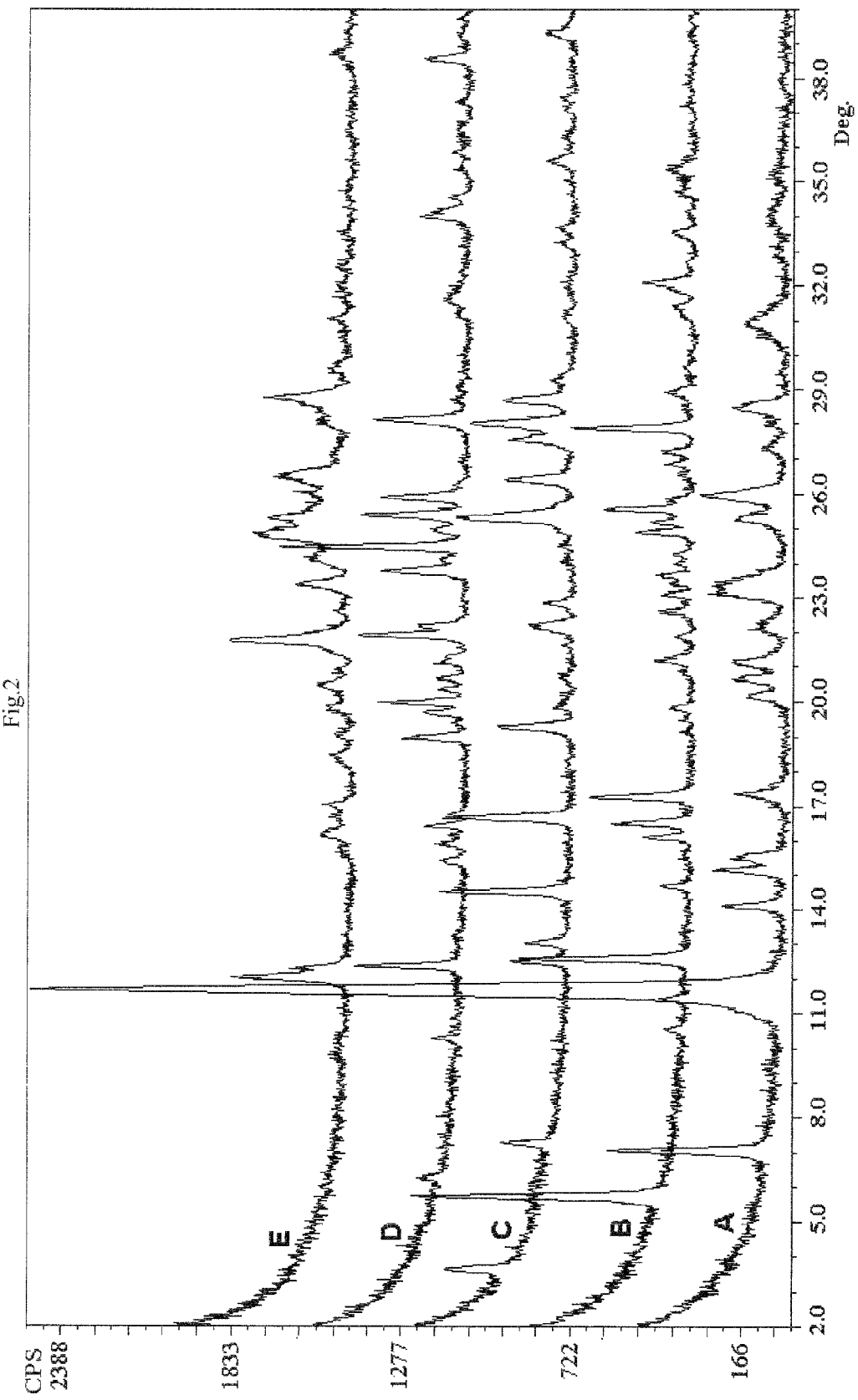
FIG. 2 shows the X-ray diffractograms of NMS-E354 free base form I (A), as reference and prepared according to example 1; maleate form I (B), hemifumarate form I (C), mesylate form I (D), sulfate form I (E) salts prepared according to example 4. The X-ray diffractogram graph reports 2-theta angles (deg) on the x axis while intensity (CPS) is reported on the y axis.

It is also stated in the preceding paragraphs that the crystalline forms of the salts and free base of NMS-E354 provide X-ray powder diffraction patterns 'substantially' the same as the X-ray powder diffraction patterns shown in FIGS. 1, 2 and 3, have substantially the most prominent peaks at the 2-theta angle values shown in tables 1, 2, 3, 4, 5 and 6. It shall be appreciated that the use of the term 'substantially' in this context is also intended to indicate that the 2-theta angle values of the X-ray powder diffraction patterns may vary slightly from one machine to another, from one sample to another, or as a result of slight variations in the applied measurement conditions, so the peak positions shown in the figures or quoted in the tables are again not to be construed as absolute values.

In this regard, it is known in the art that an X-ray powder diffraction pattern may be obtained which has one or more measurement errors depending on measurement conditions (such as equipment, sample preparation or machine used). In particular, it is generally known that intensities in an X-ray powder diffraction pattern may fluctuate depending on measurement conditions and sample preparation.

For example, persons skilled in the art of X-ray powder diffraction will realise that the relative intensity of peaks can be affected by, for example, grains above 50 microns in size and non-unitary aspect ratios, which may affect analysis of samples.

The skilled person will also realise that the position of reflections can be affected by the precise height at which the sample sits in the diffractometer and the zero calibration of the diffractometer.

The surface planarity of the sample may also have a small effect.

Hence a person skilled in the art will appreciate that the diffraction pattern data presented herein is not to be construed as absolute (for further information see "Fundamentals of Powder Diffraction and Structural Characterization, Pecharsky and Zavalij, Kluwer Academic Publishers, 2003). Therefore, it shall be understood that the crystalline form of the salts and free base of NMS-E354 described in the present invention is not limited to the crystals that provide X-ray powder diffraction patterns identical to the X-ray powder diffraction patterns shown FIGS. 1, 2 and 3 and any crystals providing X-ray powder diffraction patterns substantially the same as that shown FIGS. 1, 2 and 3 fall within the scope of the present invention.

A person skilled in the art of X-ray powder diffraction is able to judge the substantial identity of X-ray powder diffraction patterns.

Generally, a measurement error of a diffraction angle in an X-ray powder diffractogram is about 2-theta=0.5 deg or less (or, more suitably, about 2-theta=0.2 deg or less) and such degree of a measurement error should be taken into account when considering the X-ray powder diffraction pattern FIGS. 1, 2 and 3 and when interpreting the peak positions referred to both in the text and in tables 1, 2, 3, 4, 5 and 6.

Therefore, where it is stated, for example, that the salts and free base of NMS-E354 have an X-ray powder diffraction pattern with at least one specific peak at about 2-theta=5.3 deg (or any one of the other mentioned angles) then this can be interpreted as being 2-theta=5.3 deg plus or minus 0.5 deg, or 2-theta=5.3 deg plus or minus 0.2 deg.

The main X-ray diffraction peaks 2-theta angles of NMS-E354 maleate, sulfate, mesylate, hemifumarate, hydrochloride salts and the free base are described in table 1 above while the entire data sets are presented in tables 2, 3, 4, 5 and 6.

TABLE 2

NMS-E354 maleate salt

| Position (Deg.) | Intensity (CPS) | Relative Intensity (%) |
| --- | --- | --- |
| 5.8 | 1692.9 | 100.0 |
| 10.6 | 247.7 | 14.6 |
| 11.5 | 170.5 | 10.1 |
| 12.2 | 12.3 | 0.7 |
| 12.6 | 1675.2 | 99.0 |
| 14.7 | 280.0 | 16.5 |
| 15.5 | 69.7 | 4.1 |
| 16.1 | 309.8 | 18.3 |
| 16.6 | 600.2 | 35.5 |
| 17.4 | 748.9 | 44.2 |
| 19.5 | 73.4 | 4.3 |
| 19.9 | 175.7 | 10.4 |
| 20.9 | 67.5 | 4.0 |
| 21.2 | 352.9 | 20.9 |
| 22.0 | 100.1 | 5.9 |

TABLE 2-continued

NMS-E354 maleate salt

| Position (Deg.) | Intensity (CPS) | Relative Intensity (%) |
|---|---|---|
| 22.6 | 300.0 | 17.7 |
| 23.2 | 172.5 | 10.2 |
| 23.4 | 106.0 | 6.3 |
| 23.7 | 247.1 | 14.6 |
| 24.0 | 50.9 | 3.0 |
| 24.4 | 123.1 | 7.3 |
| 25.0 | 417.3 | 24.7 |
| 25.2 | 220.9 | 13.1 |
| 25.6 | 497.2 | 29.4 |
| 25.9 | 156.7 | 9.3 |
| 26.7 | 68.4 | 4.0 |
| 27.0 | 132.8 | 7.9 |
| 27.2 | 158.2 | 9.4 |
| 27.9 | 826.8 | 48.8 |
| 29.0 | 139.9 | 8.3 |
| 31.4 | 80.6 | 4.8 |
| 32.2 | 265.6 | 15.7 |
| 33.6 | 107.2 | 6.3 |
| 34.7 | 167.8 | 9.9 |
| 35.0 | 37.8 | 2.2 |
| 35.4 | 160.2 | 9.5 |
| 37.3 | 52.6 | 3.1 |
| 37.5 | 35.2 | 2.1 |
| 38.3 | 37.2 | 2.2 |
| 39.3 | 31.0 | 1.8 |

TABLE 3

NMS-E354 sulfate salt

| Position (Deg.) | Intensity (CPS) | Relative Intensity (%) |
|---|---|---|
| 12.0 | 195.0 | 32.1 |
| 12.3 | 83.1 | 13.7 |
| 16.2 | 52.0 | 8.6 |
| 16.7 | 90.2 | 14.9 |
| 17.0 | 36.4 | 6.0 |
| 18.5 | 46.0 | 7.6 |
| 19.1 | 17.9 | 3.0 |
| 19.9 | 29.3 | 4.8 |
| 20.5 | 126.5 | 20.8 |
| 21.8 | 606.7 | 100.0 |
| 23.4 | 99.9 | 16.5 |
| 24.1 | 30.1 | 5.0 |
| 24.8 | 164.2 | 27.1 |
| 25.3 | 134.8 | 22.2 |
| 25.6 | 18.0 | 3.0 |
| 26.0 | 34.7 | 5.7 |
| 26.5 | 100.6 | 16.6 |
| 28.1 | 49.5 | 8.2 |
| 28.8 | 438.3 | 72.2 |
| 29.6 | 25.3 | 4.2 |
| 31.1 | 58.5 | 9.6 |
| 38.7 | 52.2 | 8.6 |

TABLE 4

NMS-E354 mesylate salt

| Position (Deg.) | Intensity (CPS) | Relative Intensity (%) |
|---|---|---|
| 6.3 | 49.2 | 11.2 |
| 10.3 | 49.7 | 11.3 |
| 12.4 | 232.1 | 52.7 |
| 15.4 | 41.1 | 9.4 |
| 15.9 | 44.4 | 10.1 |
| 16.5 | 93.2 | 21.2 |
| 19.0 | 123.1 | 28.0 |

TABLE 4-continued

NMS-E354 mesylate salt

| Position (Deg.) | Intensity (CPS) | Relative Intensity (%) |
|---|---|---|
| 19.7 | 79.3 | 18.0 |
| 20.0 | 168.0 | 38.2 |
| 20.4 | 42.5 | 9.7 |
| 20.7 | 50.2 | 11.4 |
| 21.2 | 46.5 | 10.6 |
| 21.3 | 39.7 | 9.0 |
| 21.9 | 249.6 | 56.7 |
| 22.2 | 98.5 | 22.4 |
| 23.8 | 171.8 | 39.0 |
| 24.1 | 32.2 | 7.3 |
| 24.5 | 440.1 | 100.0 |
| 25.0 | 51.5 | 11.7 |
| 25.4 | 230.5 | 52.4 |
| 25.9 | 180.5 | 41.0 |
| 26.1 | 11.8 | 2.7 |
| 28.1 | 191.5 | 43.5 |
| 31.2 | 13.5 | 3.1 |
| 31.6 | 36.3 | 8.3 |
| 34.1 | 86.5 | 19.6 |
| 34.6 | 40.8 | 9.3 |
| 35.9 | 36.7 | 8.3 |
| 36.5 | 22.0 | 5.0 |
| 37.3 | 33.3 | 7.6 |
| 38.6 | 102.1 | 23.2 |

TABLE 5

NMS-E354 hemifumarate salt

| Position (Deg.) | Intensity (CPS) | Relative Intensity (%) |
|---|---|---|
| 3.6 | 162.3 | 56.6 |
| 7.3 | 100.8 | 35.2 |
| 12.5 | 108.6 | 37.9 |
| 13.1 | 80.4 | 28.1 |
| 14.5 | 286.6 | 100.0 |
| 16.7 | 282.8 | 98.7 |
| 19.3 | 157.9 | 55.1 |
| 19.8 | 40.8 | 14.2 |
| 20.0 | 14.1 | 4.9 |
| 20.7 | 15.4 | 5.4 |
| 22.2 | 81.1 | 28.3 |
| 22.9 | 52.9 | 18.4 |
| 25.3 | 247.3 | 86.3 |
| 26.4 | 135.0 | 47.1 |
| 27.6 | 115.8 | 40.4 |
| 28.0 | 210.6 | 73.5 |
| 28.7 | 146.6 | 51.2 |
| 29.0 | 12.3 | 4.3 |
| 29.3 | 38.9 | 13.6 |
| 29.5 | 22.9 | 8.0 |
| 31.1 | 15.3 | 5.4 |
| 31.3 | 23.1 | 8.1 |
| 32.0 | 22.6 | 7.9 |
| 33.2 | 23.6 | 8.2 |
| 33.7 | 30.0 | 10.5 |
| 35.6 | 44.3 | 15.5 |
| 37.2 | 23.2 | 8.1 |
| 37.4 | 25.3 | 8.8 |
| 39.3 | 53.0 | 18.5 |

TABLE 6

NMS-E354 free base

| Position (Deg.) | Intensity (CPS) | Relative Intensity (%) |
|---|---|---|
| 7.1 | 338.7 | 21.6 |
| 11.7 | 1567.2 | 100.0 |

TABLE 6-continued

NMS-E354 free base

| Position (Deg.) | Intensity (CPS) | Relative Intensity (%) |
|---|---|---|
| 14.1 | 121.3 | 7.7 |
| 15.2 | 134.8 | 8.6 |
| 15.5 | 96.3 | 6.1 |
| 17.0 | 26.7 | 1.7 |
| 17.3 | 85.7 | 5.5 |
| 17.6 | 30.0 | 1.9 |
| 20.2 | 66.4 | 4.2 |
| 20.7 | 89.7 | 5.7 |
| 21.2 | 95.7 | 6.1 |
| 22.1 | 41.6 | 2.7 |
| 22.3 | 29.7 | 1.9 |
| 23.1 | 77.7 | 5.0 |
| 23.4 | 120.7 | 7.7 |
| 25.3 | 87.9 | 5.6 |
| 26.0 | 157.0 | 10.0 |
| 27.3 | 30.6 | 2.0 |
| 28.0 | 47.4 | 3.0 |
| 28.5 | 97.7 | 6.2 |
| 30.9 | 66.0 | 4.2 |
| 34.0 | 20.0 | 1.3 |

Analytical Results by Means of Differential Scanning Calorimetry (DSC)

DSC analyses were carried out with a Perkin-Elmer DSC-7 apparatus. Aluminum DSC pans were loaded with about 2 mg of sample. The temperature range of the analyses was between 30° and a maximum value of 350° C.

The samples were analyzed under nitrogen flow at a heating rate of 10° C./min.

Figure 6:
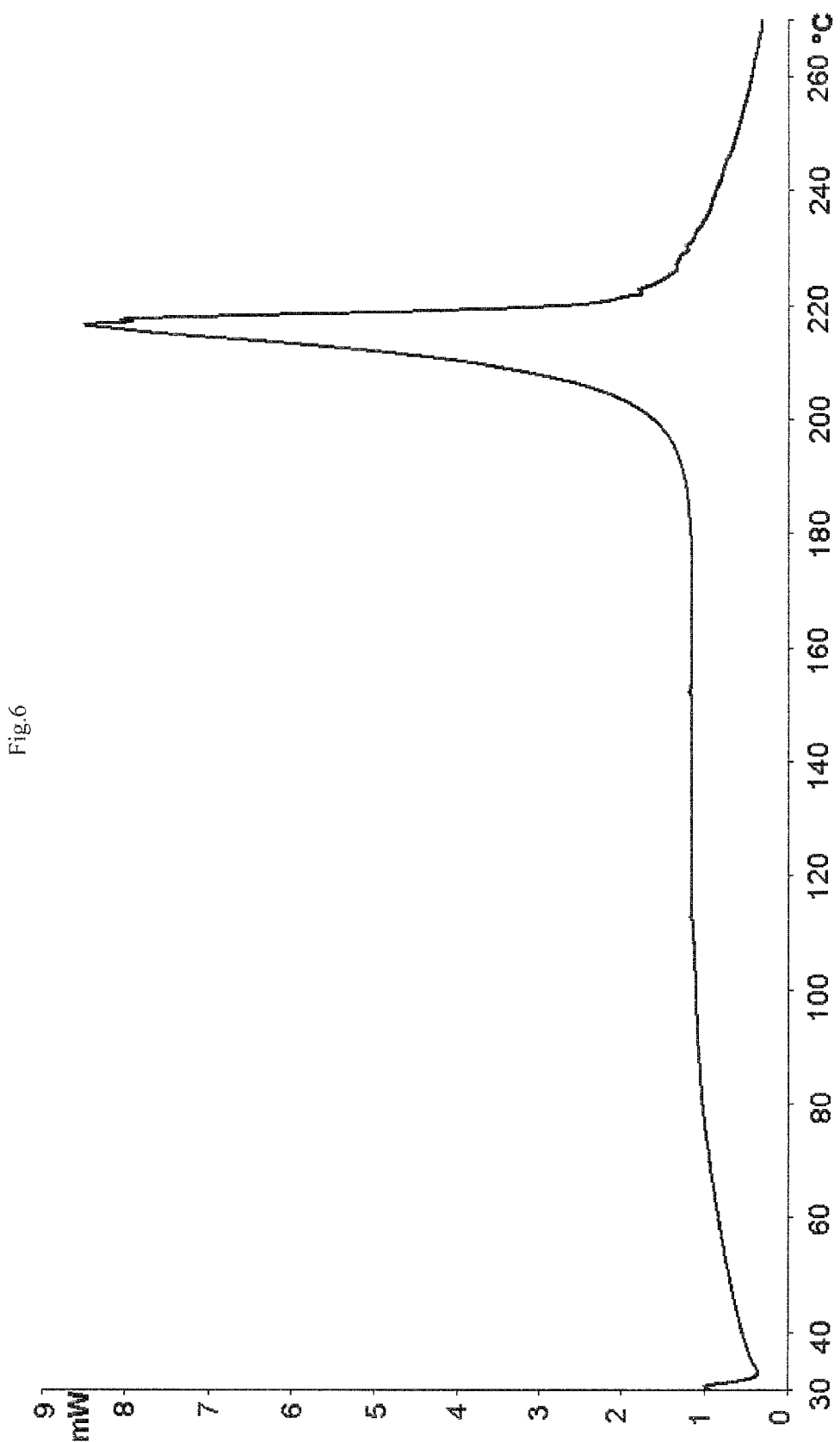
FIG. 6 reports the DSC thermogram of NMS-E354 maleate salt form I prepared according to example 5. The thermogram reports temperature (° C.) on the x axis while heat flow (mW) is reported on the y axis. New crystal forms of NMS-E354 salts selected from L-asparate, hemifumarate, hydrochloride, maleate, mesylate, phosphate, sulfate and L-tartrate salts of the present invention were found to be crystalline, rendering these forms particularly suitable for pharmaceutical development.

The observed melting endotherm of NMS-E354 maleate salt was at approximately 217° C. (peak temperature) showing ΔHf of approximately 148 J/g (see FIG. 6).

As a further aspect concerning solid state characterization by means of DSC, it has been found that NMS-E354 L-aspartate, phosphate and L-tartrate salts, characterized as crystalline materials by means of PXRD, show complex DSC profile (see FIG. 2). Such salts undergo thermal transitions involving desolvation/dehydration processes and subsequent melting of desolved/dehydrated forms characterized by their DSC melting peak temperatures. Further thermal transitions may follow when e.g. degradation occurs.

It will be understood that the onset and/or peak temperature values of the DSC may vary slightly from one machine to another, one method to another or from one sample to another, and so the values quoted are not to be construed as absolute. In fact, observed temperatures will depend on the rate of temperature change as well as sample preparation technique and the particular instrument employed. It will be estimated and taken into account that the temperature values obtained applying such different conditions may vary by plus or minus about 4° C.

Analytical Results by Means of Dynamic Vapour Sorption (DVS)

The water uptake of crystalline NMS-E354 salts and free base was investigated by submitting a sample of such substances to a hygroscopicity test by means of a DVS 1000 (SMS). The apparatus is a "controlled atmosphere microbalance" where the weighed sample is exposed to programmed variations of the relative humidity (RH) at a constant and controlled temperature. The measured parameters (weight, time and RH), reported in Excel worksheets, allow obtaining hygroscopicity curves over the tested RH range. Sorption/desorption cycles between 0% and 90% RH can be performed at controlled temperature of 25° C. Progressive variations of RH can be of 10% and 3%; they are operated by the software at the equilibration of the sample weight. This condition can be defined at a constant rate of percent weight variation e.g. 0.005%/min. The experimental results shows that the preferred NMS-E354 salts maleate, sulfate, mesylate, hemifumarate salts are characterized by low to moderate water uptakes not greater than 2%. These compounds can be considered of low hygroscopicity, showing a behavior comparable to that of the crystalline free base, a substance of low hygroscopicity when submitted to relative humidity (RH) modifications up to 90% at 25° C.

NMR Identification Analyses

The $^1$H NMR experiments were performed at a constant temperature of 28° C., on a Varian Inova 500 spectrometer operating at 499.8 MHz. A small amount of each sample was dissolved in 0.75 mL of DMSO-d6 and transferred into a 5-mm NMR tube for subsequent analysis. The analysis allows confirming the expected chemical structure of both molecule and counterions.

According to a further aspect of the invention a pharmaceutical composition can be formulated according to known method in the art in any of the pharmaceutical forms known in the art for administration to a mammal, including humans.

The person skilled in the art will appreciate from the described data and experimental examples below that the new salts of NMS-E354 described in the invention are a new, improved and valuable tool in therapy.

The pharmaceutical compositions containing the compounds of the invention are usually prepared following conventional methods and are administered in a suitable pharmaceutical form.

For example, the solid oral forms may contain, together with the active compound, diluents, e.g., lactose, dextrose, saccharose, sucrose, cellulose, corn starch or potato starch; lubricants, e.g., silica, talc, stearic acid, magnesium or calcium stearate, and/or polyethylene glycols; glidants, e.g. colloidal silicon dioxide; binding agents, e.g., starches, arabic gum, gelatine methylcellulose, carboxymethylcellulose or polyvinyl pyrrolidone; disintegrating agents, e.g., starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes. The liquid dispersions for oral administration may be, e.g., syrups, emulsions and suspensions.

As an example, the syrups may contain, as carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose, or polyvinyl alcohol.

The suspension or solutions for intramuscular injections may contain, together with the active compound, a pharmaceutically acceptable carrier, e.g., sterile water, olive oil, ethyl oleate, glycols, e.g., propylene glycol and, if desired, a suitable amount of lidocaine hydrochloride.

The solutions for intravenous injections or infusions may contain, as a carrier, sterile water or preferably they may be in the form of sterile, aqueous, isotonic, saline solutions or they may contain propylene glycol as a carrier.

The suppositories may contain, together with the active compound, a pharmaceutically acceptable carrier, e.g., cocoa butter, polyethylene glycol, a polyoxyethylene sorbitan fatty acid ester surfactant or lecithin.

For instance, a pharmaceutical composition which comprises a salt of NMS-E354, as defined herein in association with a pharmaceutically acceptable diluent or carrier.

EXAMPLES

The following Examples illustrate the invention.
Temperatures are measured in degrees Celsius (° C.).
Unless otherwise indicated, the reactions or experiments take place at room temperature.
Abbreviations:
RT: room temperature
RH: relative humidity

Example 1

Crystal Form I of NMS-E354 Free Base

A solution of the free base (prepared as described in Example 19, steps 1-3 of WO 2007 110344) in refluxing methanol (75 vol) was treated with decolorizing charcoal (10% w/w). The hot mixture was filtered and the clear filtrate was kept a +4° C. for 20 hrs. The precipitated solid was collected by filtration, washed on the filter with diethyl ether (5 vol) and dried under vacuum at +50° C. affording the crystallized product as white solid.

Example 2

NMS-E354 Maleate Salt

An aliquot of NMS-E354 free base (about 40 mg) was dissolved at room temperature in 10 mL of methanol, obtaining a nominal concentration of about 4 mg/mL.

Salt formation was performed by addition of an equimolar amount of the maleic acid dissolved in methanol to the prepared NMS-E354 free base solution at RT.

Cooling crystallization were performed at −30° C. with resting times of about 24-36 h.

The obtained precipitate was collected by vacuum filtration and dried at 40° C. under vacuum.

Example 3

NMS-E354 Salts

Operating in an analogous way of Example 2, but employing the equimolar amount of the appropriate acidic counterion in a solvent (methanol, ethanol or water), the following salts were also prepared:
NMS-E354 L-asparate salt, NMS-E354 hemifumarate salt, NMS-E354 hydrochloride salt, NMS-E354 mesylate salt, NMS-E354 phosphate salt, NMS-E354 sulfate salt and NMS-E354 L-tartrate salts.

When crystallization did not occur, the solutions were concentrated by evaporating at RT under a mild nitrogen flow to allow precipitation. In some cases, a further step of re-crystallization (e.g. compound triturated in diethylether) was required to isolate a crystalline or at least powdery sample starting from a gluey residue.

Chemical identification of NMS-E354 and acidic counterion in the obtained compounds was performed by means of $^1$H NMR as above described.

Example 4

NMS-E354 Maleate, Sulfate, Mesylate, Hemifumarate and Hydrochloride Salts

NMS-E354 free base (372 mg, 1.07 mmol) was dissolved in warm methanol (60 mL) and then allowed to cool to room temperature. The appropriate acid (1.05 equivalent), dissolved in methanol or water in the case of fumaric acid, was added under stirring. The resulting mixtures were aged at 4° C. for 48 hrs and then were concentrated to a half volume in vacuo. The solids were filtered, washed with diethyl ether and finally dried at 40° C. under vacuum affording the desired salts.

Example 5

NMS-E354 Maleate Salt 710 g of NMS-E354 free base was heated at reflux and under stirring in 60 L ethanol 95% for 20 min allowing complete dissolution of the starting material (concentration of about 12 g/L).

About 1 equivalent of maleic acid (250 g) was dissolved in 1.45 L ethanol 95% (concentration of about 170 g/L) and added to the free base solution. After 10 min at reflux (precipitation of salt started after same minutes at reflux), the heating was interrupted and the mixture allowed to decrease to about 25° C. spontaneously.

After heating interruption the mixture was stirred for about 21 hours, filtered washing with 1.5 L ethanol 95%, and then dried under vacuum with external temperature set at 50° C., 564 g of the title compound were obtained.

Example 6

Preparation of Hard Gelatin Capsules, Strength Range from 2.5 to 60 Mg.

The oral pharmaceutical compositions containing the compounds of the invention were prepared in a conventional method mixing, together with the active compound other excipients in the percentage ranges reported in Table 7.

TABLE 7

| Ingredient | Range % |
| --- | --- |
| Active compound: NMS-E354 maleate salt | 3.0 ÷ 38.0 |
| Diluent: Monohydrate Lactose | 0.0 ÷ 52.0 |
| Diluent: Pregelatinized Starch | 8.0 ÷ 97.0 |
| Lubricant: Magnesium Stearate | 0.8 ÷ 1.0 |
| Glidant: Colloidal Silicon Dioxide | 0.0 ÷ 0.7 |

The invention claimed is:

1. Crystal forms of salts of compound NMS-E354 having the formula:

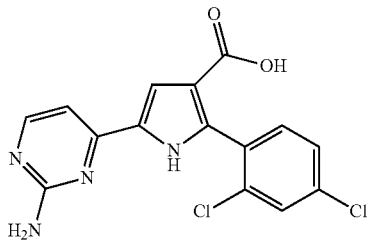 [SMILES: Nc1nccc(-c2cc(C(=O)O)c(-c3ccc(Cl)cc3Cl)[nH]2)n1]

selected from L-asparate, hemifumarate, hydrochloride, maleate, mesylate, sulfate, L-tartrate or phosphate salts, and hydrates, solvates and polymorphs thereof, having an XRD diffraction pattern substantially as shown in FIGS. 1 through 6.

2. Crystal forms of salts of compound NMS-E354 according to claim 1 selected from hemifumarate, maleate, mesylate and sulfate salts, having an XRD diffraction pattern substantially as shown in FIGS. 1 through 6.

3. Crystal forms of salts of compound NMS-E354 according to claim 1 selected from maleate and sulfate salts, having an XRD diffraction pattern substantially as shown in FIGS. 1 through 6.

4. Crystal forms of maleate salt of compound NMS-E354 according to claim 1, having an XRD diffraction pattern substantially as shown in FIGS. 1 through 6.

5. Crystal forms of the compound NMS-E354 as free base, having an XRD diffraction pattern substantially as shown in FIGS. 1, 2, 4 and 5.

6. A pharmaceutical composition comprising a crystalline form, solvate or hydrate of any salt or free base of NMS-E354 as defined in claim 1, as active ingredient and a pharmaceutically acceptable excipient and/or carrier.

* * * * *